US009835845B2

(12) United States Patent
Koshika et al.

(10) Patent No.: US 9,835,845 B2
(45) Date of Patent: Dec. 5, 2017

(54) SCANNING ENDOSCOPE

(71) Applicant: OLYMPUS CORPORATION, Tokyo (JP)

(72) Inventors: Soichiro Koshika, Mitaka (JP); Yuji Sakai, Kodaira (JP); Hiroyuki Takizawa, Chofu (JP); Daiki Ariyoshi, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/353,830

(22) Filed: Nov. 17, 2016

(65) Prior Publication Data
US 2017/0068088 A1 Mar. 9, 2017

Related U.S. Application Data

(63) Continuation of application No. PCT/JP2015/074877, filed on Sep. 1, 2015.

(30) Foreign Application Priority Data
Nov. 12, 2014 (JP) ................. 2014-229955

(51) Int. Cl.
*G02B 23/24* (2006.01)
*A61B 1/00* (2006.01)
(Continued)

(52) U.S. Cl.
CPC ............ *G02B 23/2469* (2013.01); *A61B 1/00* (2013.01); *A61B 1/0016* (2013.01);
(Continued)

(58) Field of Classification Search
CPC .. G02B 23/2469; G02B 23/2476; A61B 1/00; A61B 1/00117; A61B 1/0016;
(Continued)

(56) References Cited

U.S. PATENT DOCUMENTS

2009/0141997 A1 6/2009 Lee et al.
2010/0179386 A1 7/2010 Kobayashi
2013/0345508 A1* 12/2013 Akui ................. A61B 1/00172
600/109

FOREIGN PATENT DOCUMENTS

JP 2010-162090 A 7/2010
JP 2011-505190 A 2/2011
(Continued)

OTHER PUBLICATIONS

International Search Report dated Nov. 2, 2015 issued in PCT/JP2015/074877.
(Continued)

*Primary Examiner* — Mary Ellen Bowman
(74) *Attorney, Agent, or Firm* — Scully, Scott, Murphy & Presser, P.C.

(57) ABSTRACT

A scanning endoscope includes: a light guide portion configured to guide an illuminating light that is emitted from a light source portion and irradiate an object with the illuminating light; an actuator configured to drive so as to cause a distal end of a light guide portion to scan, in order to scan the guided illuminating light over an object; a holding portion configured to hold the actuator; a rigid tubular member having a space that encloses the light guide portion, the actuator and the holding portion; and a connection portion that is interposed between the tubular member and the holding portion, and is configured to hold the holding portion at a prescribed position within the tubular member and to change shape in a circumferential direction that takes a longitudinal direction of the light guide portion as an axis when the tubular member or holding portion receives a force.

8 Claims, 12 Drawing Sheets

(51) Int. Cl.
  *A61B 1/04* (2006.01)
  *A61B 1/06* (2006.01)
  *H04N 5/225* (2006.01)

(52) U.S. Cl.
  CPC ............ *A61B 1/00117* (2013.01); *A61B 1/04* (2013.01); *A61B 1/06* (2013.01); *G02B 23/2476* (2013.01); *H04N 5/2256* (2013.01); *H04N 2005/2255* (2013.01)

(58) Field of Classification Search
  CPC .......... A61B 1/04; A61B 1/06; H04N 5/2256; H04N 2005/2255
  See application file for complete search history.

(56) References Cited

FOREIGN PATENT DOCUMENTS

| | | |
|---|---|---|
| JP | 2012-078733 A | 4/2012 |
| JP | 2014-079283 A | 5/2014 |
| WO | WO 2009/070151 A1 | 6/2009 |
| WO | WO 2013/089053 A1 | 6/2013 |

OTHER PUBLICATIONS

Japanese Office Action dated May 10, 2016 issued in Japanese Patent Application No. 2016-504245.

\* cited by examiner

FIG. 11C

SCANNING ENDOSCOPE

CROSS REFERENCE TO RELATED APPLICATION

This application is a continuation application of PCT/JP2015/074877 filed on Sep. 1, 2015 and claims benefit of Japanese Application No. 2014-229955 filed in Japan on Nov. 12, 2014, the entire contents of which are incorporated herein by this reference.

BACKGROUND OF THE INVENTION

1. Field of the Invention

The present invention relates to a scanning endoscope that scans an illuminating light and acquires an endoscopic image.

2. Description of the Related Art

Endoscopes that scan an illuminating light are being widely used in a medical field and the like. A scanning endoscope has also been proposed that two-dimensionally scans a light that has been guided by an optical fiber over an object such as an observation site, and receives reflected light from the object and generates an image.

For example, a conventional example described in Japanese Patent Application Laid-Open Publication No. 2012-78733 discloses a scanning-type confocal endoscope apparatus configured to condense, by means of a lens unit, a laser beam emitted from an optical fiber as a light guiding member that is swung by an actuator. In this conventional example, the lens unit is fixed to a distal end, and an internal cylinder having a mount that holds the actuator fixed at a position that is partway along the internal cylinder is slidably disposed with respect to an external cylinder, and is moved in a Z-axis direction by a Z-axis actuator disposed on the proximal end side of the internal cylinder. A structure is disclosed in which a member holding the Z-axis actuator is fixed (connected) to the external cylinder in a manner in which one part of an outer circumferential portion of the member is notched.

SUMMARY OF THE INVENTION

A scanning endoscope according to one aspect of the present invention includes: a light guide portion configured to guide an illuminating light that is emitted from a light source portion, and irradiate an object with the illuminating light; an actuator configured to drive so as to cause a distal end of the light guide portion to scan, in order to scan the illuminating light that is guided from the light guide portion over the object; a holding portion that is connected to the actuator and is configured to hold the actuator; a rigid tubular member having a space that encloses the light guide portion, the actuator and the holding portion; and a connection portion that is interposed between the tubular member and the holding portion and is configured to hold the holding portion at a prescribed position inside the tubular member, and which changes shape in a circumferential direction which takes a longitudinal direction of the light guide portion as an axis when the tubular member or the holding portion receives a force.

BRIEF DESCRIPTION OF THE DRAWINGS

FIG. 11C is a view illustrating a seventh modification by means of a tabular format.

DETAILED DESCRIPTION OF THE PREFERRED EMBODIMENTS

Embodiments of the present invention are described hereunder with reference to the drawings.

First Embodiment

Figure 1:
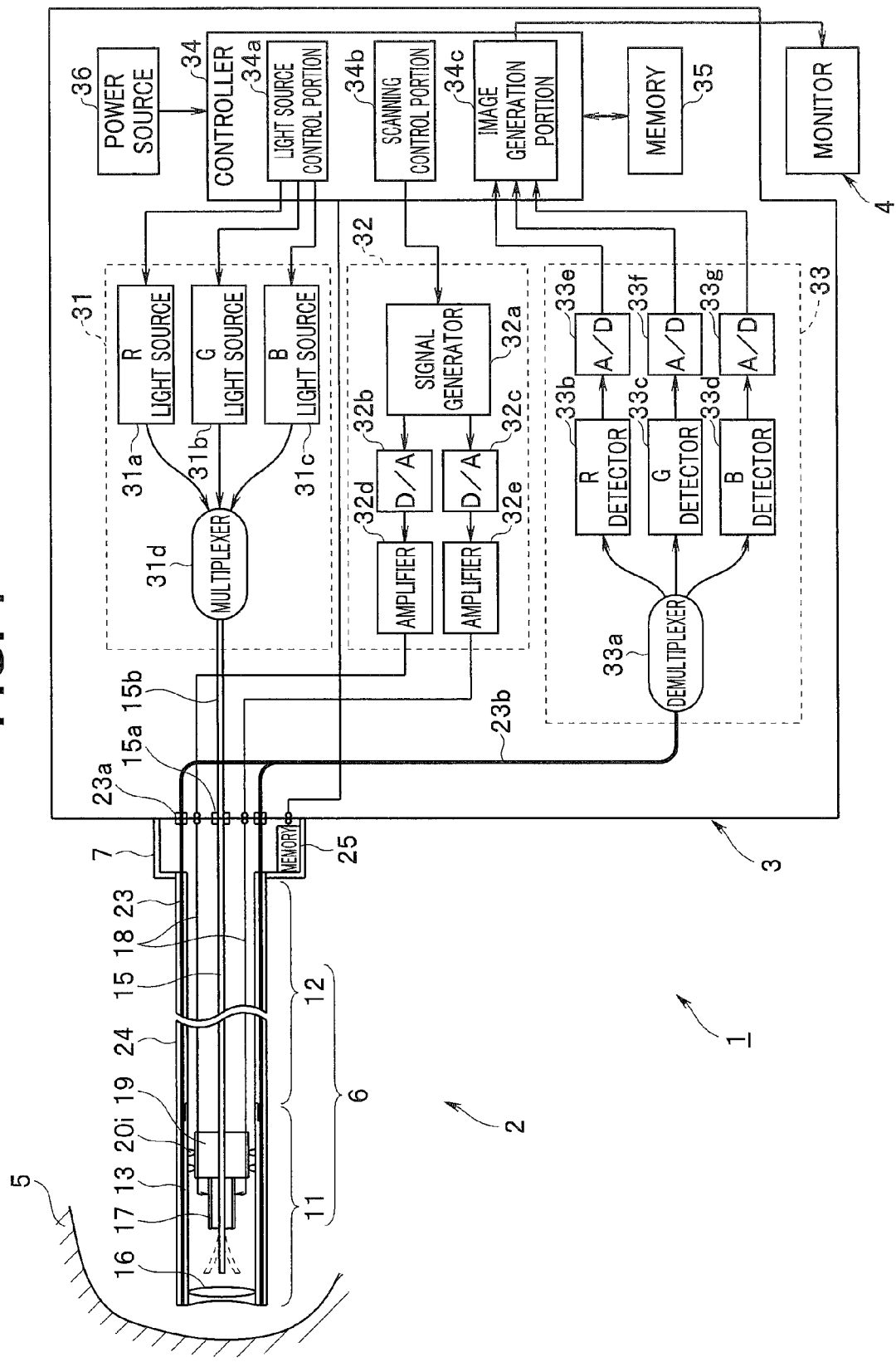
FIG. 1 is a view illustrating an overall configuration of a scanning endoscope apparatus equipped with a first embodiment of the present invention.

As illustrated in FIG. 1, a scanning endoscope apparatus 1 includes a scanning endoscope 2 of a first embodiment of the present invention, a main body apparatus (or scanning endoscope control apparatus) 3 to which the scanning endoscope 2 is detachably connected, and a monitor 4 as a display apparatus that is connected to the main body apparatus 3.

The scanning endoscope 2 has an insertion portion 6 which has an elongated shape and flexibility and which is insertable into the body or a body cavity of a subject 5. A connector 7 for detachably connecting the scanning endoscope 2 to the main body apparatus 3 is provided at a proximal end (rear end) of the insertion portion 6.

The insertion portion 6 also has a rigid distal end portion 11, and a flexible tube portion 12 that has flexibility and which extends from the rear end of the distal end portion 11 to the connector 7. Note that a configuration may be adopted in which a bendable bending portion is provided between the distal end portion 11 and the flexible tube portion 12, and an operation portion on which operation knobs or the like are provided for bending the bending portion is provided between the flexible tube portion 12 and the connector 7.

The distal end portion 11 has a cylindrical member 13 as a rigid tubular member. A distal end of a flexible cylindrical tube 14 is connected to a rear end of the cylindrical member 13. The connector 7 is fixed to a rear end of the cylindrical tube 14.

An optical fiber 15 which forms a light guiding member that guides an illuminating light is inserted through the inside of the insertion portion 6. A proximal end (rear end) of the optical fiber is connected at an optical connection portion 15a in the connector 7 to an optical fiber 15b which is provided inside the main body apparatus 3. An illuminating light that is generated at a light source unit 31 inside the main body apparatus 3 passes through the optical fiber 15b and is incident on a proximal end of the optical fiber 15. The illuminating light that is guided by the optical fiber 15 travels from a distal end face of the optical fiber 15 via an illumination lens 16 which converges the light that is mounted at a distal end of the cylindrical member 13 that faces the distal end face, and is emitted toward an object such as an inspection site inside the subject 5.

Figure 2:
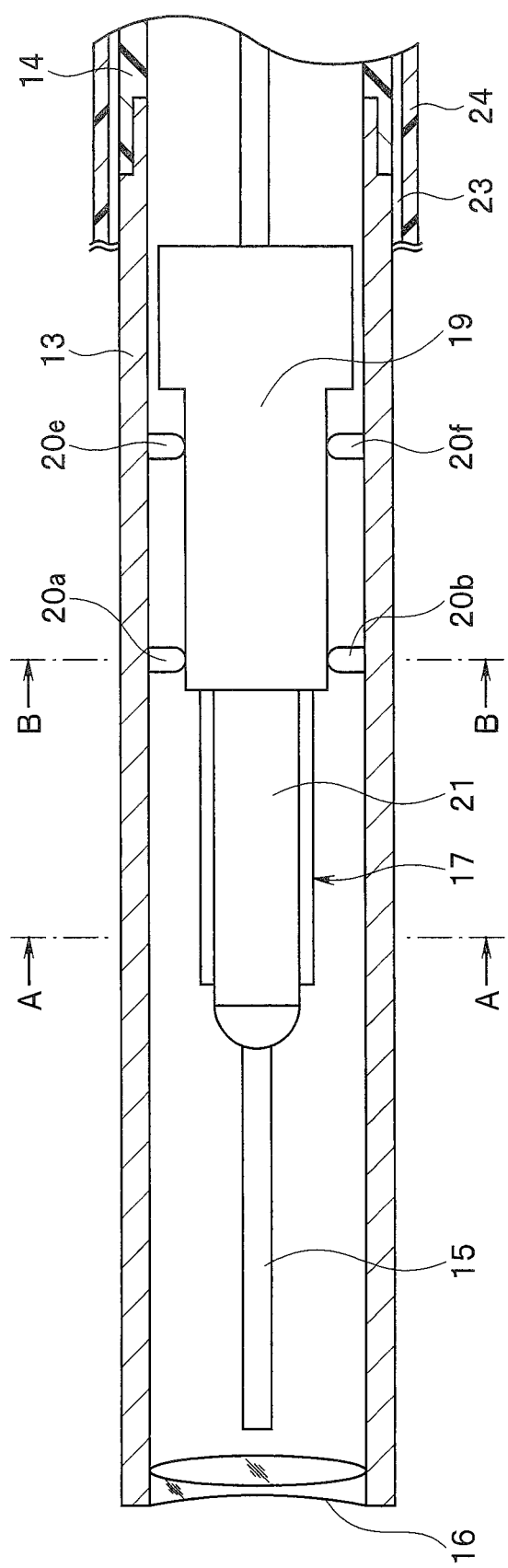
FIG. 2 is a longitudinal cross-sectional view illustrating the internal configuration of a cylindrical member in a scanning endoscope of the first embodiment.

As also shown in FIG. 2, inside the cylindrical member 13 forming the distal end portion 11, an actuator 17 is disposed that forms a driving portion configured to drive a distal end side of the optical fiber 15 so as to swing in a direction that is orthogonal to a longitudinal direction of the optical fiber 15. Driving signals from a driving unit 22 provided inside the main body apparatus 3 are applied to the actuator 17 through drive wires 18 that are inserted through the inside of the insertion portion 6.

The (proximal end of the) actuator 17 is held by a holding member 19 that forms a holding portion configured to hold the actuator 17. The holding member 19 is held by a plurality of connection members 20i (in the present embodiment, i=a to d, and e to h) that are provided in the cylindrical member 13. In the example illustrated in FIG. 2, the proximal end side of the holding member 19 is formed with a large diameter in a stepped shape to form a large-diameter portion to thereby provide a small air-gap portion between the holding member 19 and the cylindrical member 13, and thus the occurrence of vibrations with a large amplitude that exceeds the space of the air-gap portion in one of the two members is suppressed.

Note that the connection members 20i may also be defined as second holding members that hold the holding member 19. In such case, the holding member 19 that holds the actuator 17 may be defined as a first holding member or an actuator holding member.

Figure 3:
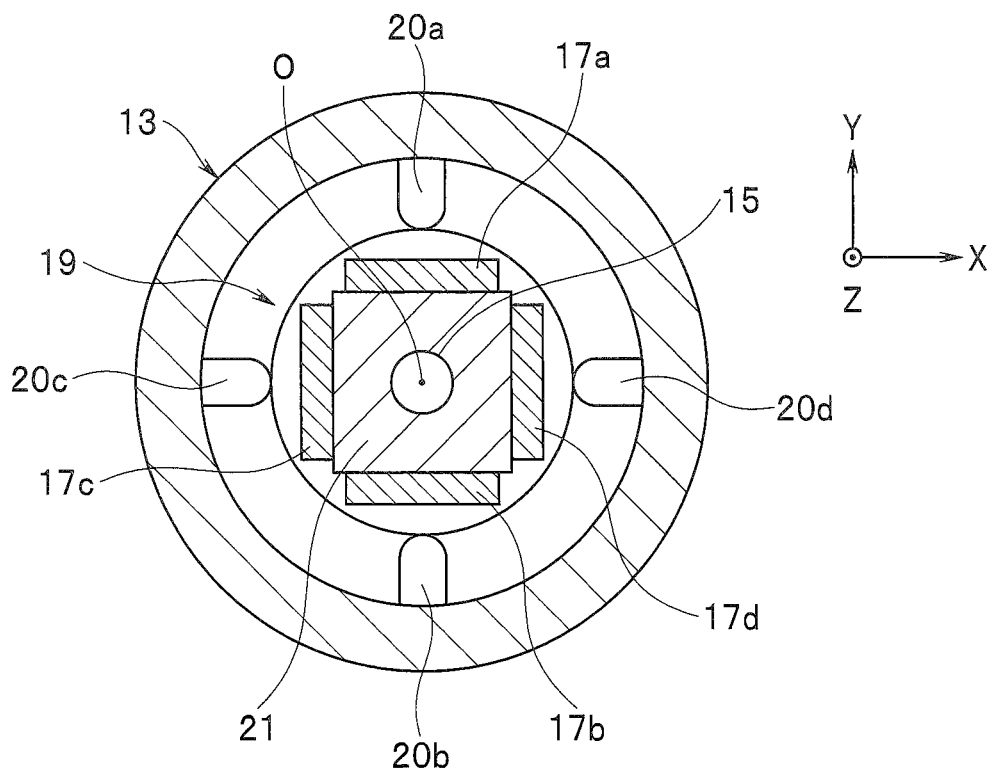
FIG. 3 is an enlarged cross-sectional view along a line A-A in FIG. 2.

As shown in FIG. 2 and FIG. 3, inside the cylindrical member 13, between the optical fiber 15 and actuator elements 17a to 17d that form the actuator 17 is disposed a ferrule 21 as a rigid bonding member that bonds the aforementioned two components (that is, the optical fiber 15 and the actuator 17). Specifically, the ferrule 21 is formed of, for example, zirconia (ceramic) or nickel.

As illustrated in the transverse cross section in FIG. 3, the ferrule 21 is formed in a quadrangular prism shape, the optical fiber 15 is fixed along the central axis, and the actuator elements 17a and 17b, and 17c and 17d are attached to both side faces in the Y-axis direction (vertical direction on the paper surface) and both side faces in the X-axis direction (lateral direction on the paper surface), respectively.

Each actuator element is, for example, constituted by a piezoelectric element, and is configured to expand and contract in a longitudinal direction (Z-axis direction in FIG. 3) upon application of a driving signal to the actuator element. Therefore, in a state in which the proximal end of the optical fiber 15 is held, the distal end side of the optical fiber 15 can be caused to swing in the vertical direction as indicated by dashed lines in FIG. 1 by application of, for example, driving signals of opposite phases to the actuator elements 17a and 17b (to expand one and contract the other).

The proximal ends of the actuator elements 17a to 17d are held by the cylindrically shaped holding member 19. The holding member 19 is held by rigid connection members 20a to 20d, and 20e to 20h (represented by "20i" in some cases) which form connection portions that project towards the center in the radial direction from the inner circumferential face of the cylindrical member 13.

As shown in FIG. 1, a plurality of light-receiving optical fibers 23 for receiving illuminating light reflected by the object are disposed in a ring shape along an outer circumferential face of the cylindrical member 13 and the cylindrical tube 14. Light (return light or reflected light from the object) received by the light-receiving optical fibers 23 is guided to a light-receiving optical fiber 23b inside the main body apparatus 3 via an optical connection portion 23a of the connector 7. The light that is guided to the light-receiving optical fiber 23b enters a detection unit 33 and is converted to an electrical signal.

The light-receiving optical fibers 23 that are disposed in a ring shape are covered and protected by an exterior member 24.

Each scanning endoscope 2 has a memory 25 that stores information such as driving data for driving the distal end of the optical fiber 15 along a predetermined scanning pattern by means of the actuator 17 and coordinate position data corresponding to irradiation positions when the distal end of the optical fiber 15 is driven. The information stored in the memory 25 is inputted to a controller 34 inside the main body apparatus 3 via a contact of the connector 7 and a signal wire.

The main body apparatus 3 includes the light source unit 31, the driving unit 32, the detection unit 33, the controller 34 configured to control each unit of the main body apparatus 3, a memory 35 that is connected to the controller 34 and stores various kinds of information, and a power source (circuit) 36 that supplies direct-current power to the controller 34 and the like.

The light source unit 31 has an R light source 31a configured to generate light in the red wavelength band (hereinafter also referred to as "R light"), a G light source 31b configured to generate light in the green wavelength band (hereinafter also referred to as "G light"), a B light source 31c configured to generate light in the blue wavelength band (hereinafter also referred to as "B light"), and a multiplexer 31d configured to multiplex (mix) the R light, G light and B light.

The R light source 31a, G light source 31b and B light source 31c are constituted using, for example, laser light sources, and emit the R light, the G light and the B light to the multiplexer 31d, respectively, when turned on by control of the controller 34. The controller 34 includes a light source control portion 34*a* constituted by a central processing unit (abbreviated as "CPU") or the like that is configured to control discrete light emission of the R light source 31*a*, the G light source 31*b* and the B light source 31*c*.

The light source control portion 34*a* of the controller 34 transmits control signals for simultaneous and pulsed light emission to the R light source 31*a*, the G light source 31*b*, and the B light source 31*c*, and the R light source 31*a*, the G light source 31*b*, and the B light source 31*c* simultaneously generate the R light, the G light, and the B light and emit the R light, the G light, and the B light to the multiplexer 31*d*.

The multiplexer 31*d* multiplexes the R light from the R light source 31*a*, the G light from the G light source 31*b*, and the B light from the B light source 31*c* and supplies the light to a light incident face of the optical fiber 15*b*. The optical fiber 15*b* supplies the multiplexed R light, G light, and B light as illuminating light to the optical fiber 15.

The driving unit 32 has a signal generator 32*a*, D/A converters 32*b* and 32*c*, and amplifiers 32*d* and 32*e*.

The signal generator 32*a* is configured to generate driving signals for moving (or swinging) a light-emission end portion of the distal end of the optical fiber 15 and to output the driving signals to the D/A converters 32*b* and 32*c* based on control of a scanning control portion 34*b* of the controller 34. The D/A converters 32*b* and 32*c* convert digital driving signals that are outputted from the signal generator 32*a* to analog driving signals and output the analog driving signals to the amplifiers 32*d* and 32*e*, respectively.

Figure 4A:
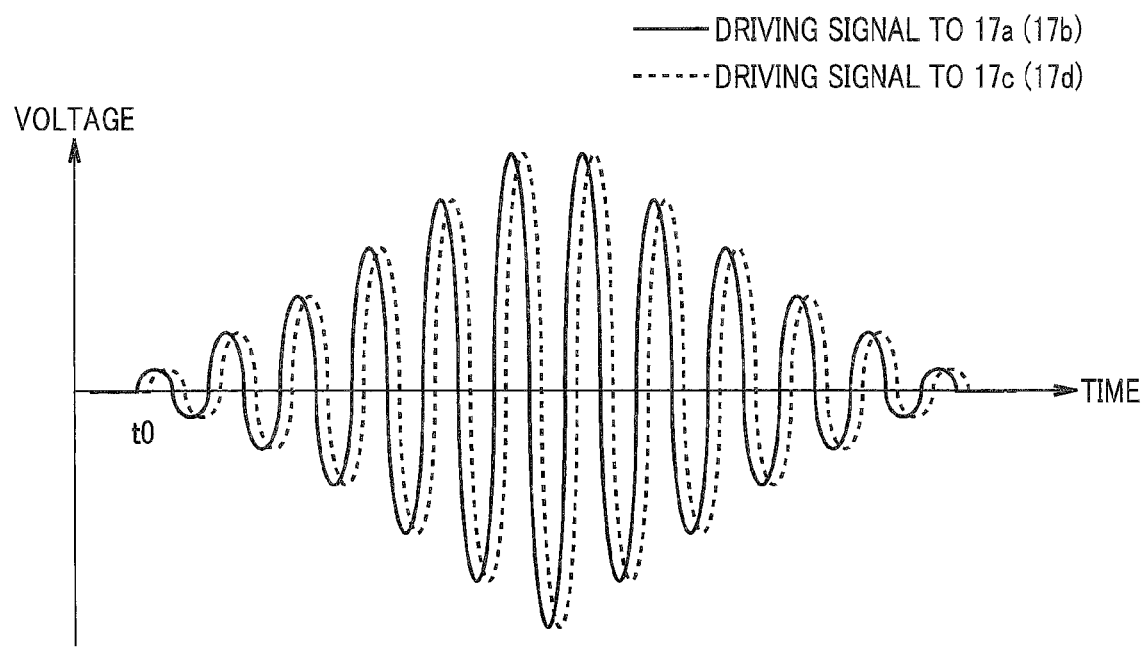
FIG. 4A is a view illustrating waveforms of driving signals that drive an actuator.

The amplifiers 32*d* and 32*e* amplify the respective driving signals outputted from the D/A converters 32*b* and 32*c*, and output driving signals having the waveforms shown in FIG. 4A to the actuator 17.

Figure 4B:
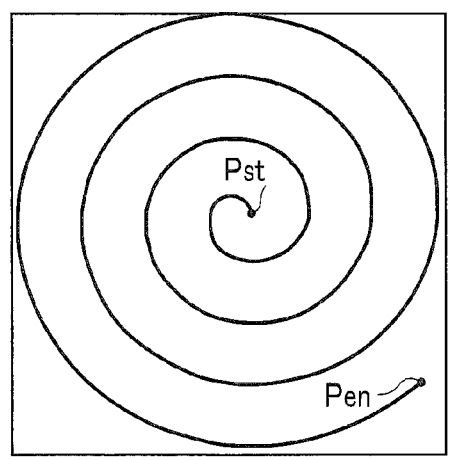
FIG. 4B is a view illustrating a trajectory along which a distal end of an optical fiber is swung by the driving signals in FIG. 4A.

The distal end of the optical fiber 15 is swung so as to form a spiral scanning trajectory as shown in FIG. 4B.

The detection unit 33 includes a demultiplexer 33*a*, detectors 33*b*, 33*c* and 33*d*, and A/D converters 33*e*, 33*f* and 33*g*.

The demultiplexer 33*a* includes a dichroic mirror and the like, and is configured to split return light emitted from a light emission end face of the light-receiving optical fiber 23*b* into light of the respective color components of R (red), G (green) and B (blue), and to emit the light of the respective color components to the detectors 33*b*, 33*c* and 33*d*.

The detectors 33*b*, 33*c* and 33*d* are constituted by photodetectors, such as photodiodes, and detect an intensity of the R light, an intensity of the G light, and an intensity of the B light outputted from the demultiplexer 33*a*, respectively, generate analog R, G, and B detection signals corresponding to the detected intensities of the R light, the G light, and the B light, respectively, and output the signals to the A/D converters 33*e*, 33*f*, and 33*g*.

The A/D converters 33*e*, 33*f*, and 33*g* convert the analog R, G, and B detection signals respectively outputted from the detectors 33*b*, 33*c* and 33*d* into digital R, G, and B detection signals, respectively, and output the signals to an image generation portion 34*c* configured to generate an image that is provided inside the controller 34.

A control program and the like for performing control of the main body apparatus 3 are stored in the memory 35 in advance. Information regarding coordinate positions that is read from the memory 25 is also stored in the memory 35 by the controller 34 of the main body apparatus 3.

The controller 34 is constituted using a CPU or the like, and is configured to read out a control program stored in the memory 35 and perform control of the light source unit 31 and the driving unit 32 based on the control program that is read out.

Figure 5A:
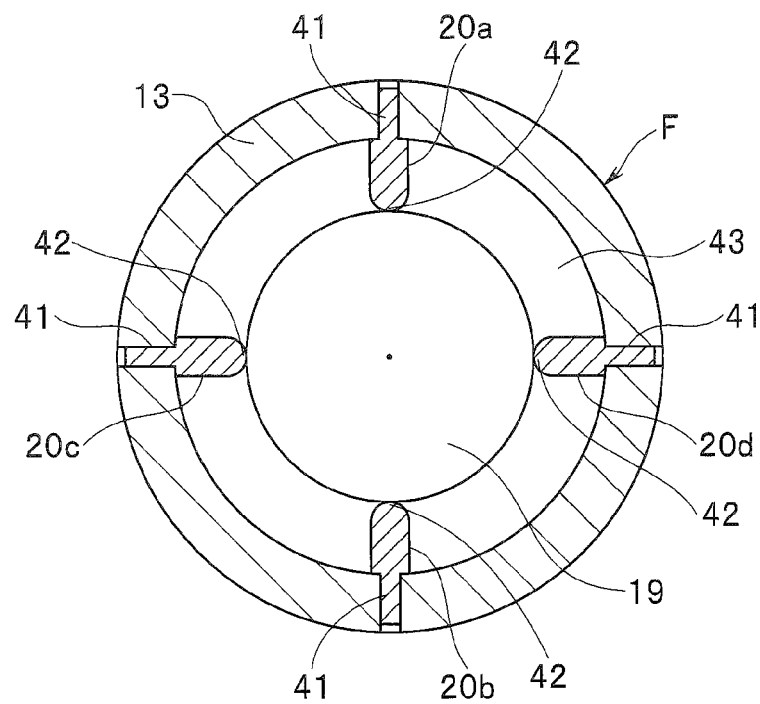
FIG. 5A is a view illustrating, in an enlarged manner, the cylindrical member and a holding member shown in FIG. 2, as well as connection portions that are interposed between the cylindrical member and the holding member.
Figure 5B:
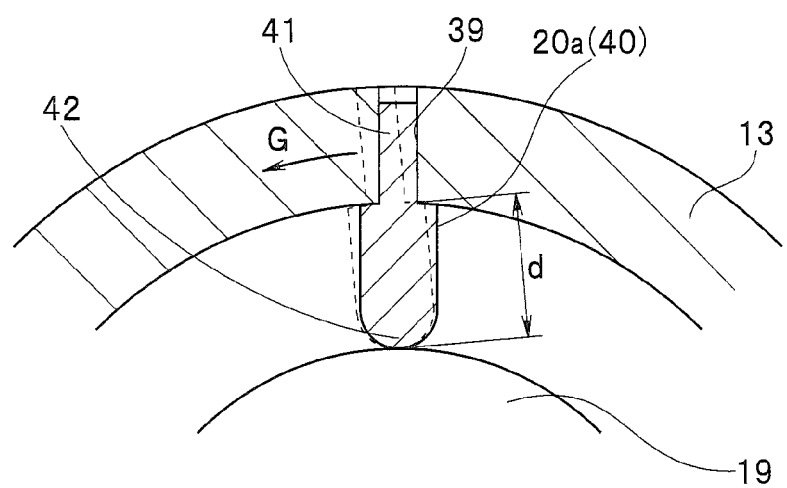
FIG. 5B is an enlarged view illustrating a portion of FIG. 5A in an enlarged manner.

FIG. 5A illustrates, in an enlarged manner, a connection member periphery portion by means of a cross-section along a line B-B in FIG. 2, and from which the internal configuration of the holding member 19 which is illustrated in FIG. 3 is omitted. FIG. 5B illustrates, in an enlarged manner, the peripheral portion of the connection member 20*a* shown in FIG. 5A.

In the configuration example shown in FIG. 5A, four holes for positioning (denoted by reference numeral 39 in FIG. 5B) are provided at a first prescribed location and a second prescribed location, respectively, in the outer circumferential face of the cylindrical member 13. The first prescribed location and a second prescribed location are at two predetermined distances along the longitudinal direction from the distal end position of the cylindrical member 13. Further a configuration is adopted so that, for example, the proximal end sides of the cylindrical connection members 20*a* to 20*d* and 20*e* to 20*h* are inserted into the holes for positioning, and the (proximal end sides of the) connection members 20*a* to 20*d* and 20*e* to 20*h* are fixed with an adhesive or the like to the cylindrical member 13, and the holding member 19 disposed inside the cylindrical member 13 is held by the protruding distal end portions of the connection members 20*a* to 20*d* and 20*e* to 20*h*.

FIG. 5A illustrates the connection members 20*a* to 20*d* at the first prescribed location that is at the front side in the longitudinal direction of the cylindrical member 13. The connection members 20*e* to 20*h* are provided in a similar manner to the connection members 20*a* to 20*d* at the second prescribed location that is on the rearward side relative to the first prescribed location.

As shown in FIG. 5A and FIG. 5B, in each connection member 20*i*, a small-diameter shaft portion 41 is provided that is made by forming a proximal end side of a shaft portion 40 (simplified and shown only in FIG. 5B) to have a small diameter in a stepped shape, and the small-diameter shaft portion 41 is set to have an external diameter such that the small-diameter shaft portion 41 engages in the hole in the cylindrical member 13. Further, in each connection member 20*i*, a convex distal end portion 42 that is rotationally symmetric about the central axis of the corresponding connection member 20*i* is provided at a distal end of the shaft portion 40 that protrudes to the inner side of the cylindrical member 13. Note that the shaft portion 40 is also rotationally symmetric about the central axis of the shaft portion 40.

The convex distal end portion 42 is a convex shape in which the distal end along the central axis projects most, and the convex distal end portion 42 may be formed in a hemispherical shape as described later. The aforementioned holes in the cylindrical member 13 are formed along radial directions that are orthogonal to a central axis O of the cylindrical member 13. Further, the holding member 19 is held so that the optical fiber 15 is disposed along the central axis O. That is, the distal end portion 11 of the insertion portion 6 is formed so that the central axis of the optical fiber 15 and the central axis of the holding member 19 along the central axis O of the cylindrical member 13 coincide with each other.

In the present embodiment, the convex distal end portion 42 is provided on the distal end side of each connection member 20*i*, and as shown in FIG. 5A and FIG. 5B, the convex distal end portions 42 hold the holding member 19 in a state that is close to substantially point contact (that is, a state of contact or abutment with a narrow area) at positions at four places (specifically, four places on the top, bottom, left and right on the cylindrical outer circumferential face) which are rotationally symmetric about the central axis O.

By adopting a configuration so that the directions in which a holding power acts in a case where the convex distal end portion 42 of each connection member 20i abuts against and holds the holding member 19 as shown in FIG. 5A are such that the holding power acts on a single point on the central axis O of the holding member 19 from directions orthogonal to the central axis O, the cylindrical holding member 19 is held so that the center of the cylindrical holding member 19 is positioned on the central axis O. That is, a configuration is adopted that holds the holding member 19 so that the center of the holding member 19 is positioned on the central axis O in a state that is close to substantially point contact by the plurality of connection members (specifically, the four connection members 20a to 20d) provided at a plurality of positions that are rotationally symmetric with respect to the central axis O.

Further, by holding the holding member 19 in the state that is close to point contact in this way, a wide space 43 is formed which, in case where a vibration is applied to the cylindrical member 13, serves as a vibration relief portion in which a major part of the vibration excluding a vibration component that acts in the central axis direction of each connection member 20i does not act on the holding member 19. In the example illustrated in FIG. 5A, in the cylindrical space between the outer circumference of the holding member 19 and the inner circumference of the cylindrical member 13, the wide space 43 that accounts for a proportion of the cylindrical space that is several times greater than the proportion of the cylindrical space occupied by the plurality of connection members (specifically, the four connection member 20a to 20d) is formed around the holding regions in which the plurality of connection members hold the holding member 19 from four directions.

Further, in FIG. 5A, if a vibration is applied to the cylindrical member 13 from, for example, the direction denoted by reference character F, although the cylindrical member 13 at that portion vibrates, because a connection member 20i is not provided in a direction that is close to the direction F, vibration of the holding member 19 on the inner side of the cylindrical member 13 can be suppressed or lessened.

Furthermore, since the holding member 19 is being held by the connection members (specifically, the connection members 20a to 20d and 20e to 20h) respectively at a plurality of places that are rotationally symmetric in the circumferential direction at the two places that are the first and second prescribed locations in the longitudinal direction of the cylindrical member 13 as described above, in comparison to a case of holding the holding member 19 from multiple directions at outer circumference positions at one location in the longitudinal direction, the holding member 19 can be held so as to maintain a position along the central axis O of the cylindrical member 13.

Further, in the present embodiment, as described above, a configuration is adopted in which, in a state that is close to substantially point contact by the plurality of connection members 20a to 20d and 20e to 20h, the holding member 19 is held so that the center of the holding member 19 is positioned on the central axis O, and even if an operation is performed such that a rotational displacement (including a case of a rotational vibration) at a rapid speed occurs around the central axis O of the cylindrical member 13, the configuration is such that the occurrence of a situation in which the rapid rotational displacement to the cylindrical member 13 is transmitted to the holding member 19 can be reduced or suppressed.

Specifically, as shown in FIG. 5B, in a case where, for example, on the cylindrical member 13 side, a rotational displacement in a direction indicated by an arrow G occurs at a rapid speed, although the connection member 20a on the cylindrical member 13 side moves or changes position in accordance with the displacement, (in comparison to a case where the connection member 20a is caused to abut with a wide area) it is difficult for a force that causes a displacement to be transmitted to the holding member 19 that is held in an abutting state with a narrow area that is close to point contact by the convex distal end portion 42, and therefore a rapid displacement of the holding member 19 can be suppressed.

Note that, in the present specification, a rotational displacement at a rapid speed means a displacement in the case of a comparison with a frame period in which an image for a single frame is acquired. Although in FIG. 5B, a case is illustrated in which the cylindrical member 13 side undergoes a rotational displacement, in a case where the holding member 19 side undergoes a rapid rotational displacement, it is similarly difficult for the displacement to be transmitted to the cylindrical member 13 side and a rotational displacement of the cylindrical member 13 can be reduced or suppressed.

The connection member 20a and the like forming the connection portions are interposed between the tubular member and the holding portion, and hold the holding portion at a prescribed position inside the tubular member, and can be said to have a function that changes shape in response to the rotation when the tubular member or the holding portion rotates taking the longitudinal direction of (the optical fiber 15 forming) the light guide portion as an axis.

The scanning endoscope 2 of the present embodiment includes: the optical fiber 15 forming a light guide portion configured to guide an illuminating light emitted from the light source unit 31 forming a light source portion, and irradiate an object with the illuminating light; the actuator 17 configured to drive so as to cause the distal end of the light guide portion to scan, in order to scan the illuminating light that is guided from the light guide portion over the object; the holding member 19 forming a holding portion that is connected to the actuator 17 and is configured to hold the actuator 17; the cylindrical member 13 forming a rigid tubular member having a space that encloses the light guide portion, the actuator 17, and the holding portion; and the connection members 20a to 20h forming connection portions that are interposed between the tubular member and the holding portion and are configured to hold the holding portion at a prescribed position inside the tubular member, and which change shape in a circumferential direction which takes the longitudinal direction of the light guide portion as an axis when the tubular member or the holding portion receives a force.

The actions of the scanning endoscope 2 configured as described above will now be described.

When the scanning endoscope 2 is connected to the main body apparatus 3 and enters an operating state, the controller 34 reads out information from the memory 23 and stores the information in the memory 35. Further, the scanning control portion 34b of the controller 34 controls so as to apply driving signals to the actuator 17 from the driving unit 32. By application of the driving signals to the actuator 17, the actuator 17 scans (swings) the distal end side of the optical fiber 15 in a spiral shape from a scanning start position Pst to a scanning end position Pen that are illustrated in FIG. 4B.

Further, the light source control portion 34a of the controller 34 controls so as to cause the light source unit 31 to discretely emit pulsed light sequentially at predetermined coordinate positions. The detection unit 33 sequentially samples return light from the subject 5 side when the pulsed light is discretely emitted, and acquires a detection signal. The detection unit 33 sends the acquired detection signal to the image generation portion 34c, and the image generation portion 34c temporarily stores the inputted detection signal in, for example, the memory 35.

The image generation portion 34c of the controller 34 converts image information constituted by the detection signal stored in the memory 35 and information regarding the position of the pulsed light when the detection signal is acquired into a standard image signal for a case where raster scanning is performed, and outputs the resultant image signal to the monitor 4. An endoscopic image is then displayed on the monitor 4.

The endoscopic image displayed on the monitor 4 is acquired by swinging the distal end of the optical fiber 15 forming the light guide portion in an X-axis and Y-axis direction that are directions which are orthogonal to the central axis O by means of the actuator 17 in a predetermined holding state in which the proximal end side of the actuator 17 is held in a condition in which the central axis of the holding member 19 and the central axis of the optical fiber 15 are set on the central axis O of the cylindrical member 13.

In the predetermined holding state in which the central axis of the holding member 19 that holds the proximal end side of the actuator 17 is held on the central axis O as described above, if a vibration is applied to the cylindrical member 13, the vibration is transmitted through the connection members 20a to 20d and 20e to 20h to the holding member 19 on the inner side of the cylindrical member 13, and the vibration affects image information that is acquired in a case where the distal end of the optical fiber 15 is swung in the predetermined holding state.

In the present embodiment, since a configuration is adopted so as to hold the holding member 19 by means of the connection members 20a to 20d and 20e to 20h that are provided between the cylindrical member 13 and the holding member 19 disposed on the inner side of the cylindrical member 13 at four positions on the top, bottom, left and right at locations in the circumferential directions that are at a first and a second distance from the end portion along the longitudinal direction, as shown in FIG. 5A the holding member 19 can be made less susceptible to the influence of vibrations in comparison to a case of holding the holding member 19 at consecutive positions in the circumferential direction. Note that in a case where a surgeon inserts the insertion portion 6 into a body cavity, if the surgeon performs an operation to rotate the cylindrical tube 14 forming the insertion portion 6 in a direction about the longitudinal direction of the cylindrical tube 14, although a rotational displacement occurs whereby the cylindrical member 13 on the distal end side of the cylindrical tube 14 also rotates in a direction about the longitudinal direction (in other words, around the central axis O), in this case, with respect to a rapid rotational displacement, as described above referring to FIG. 5B, by forming the convex distal end portion 42 at the distal end of each of the connection members 20a to 20d and 20e to 20h, a rotational displacement amount on the holding member 19 side can be suppressed or reduced.

Further, in the present embodiment, as shown in FIG. 5B, for example, since the small-diameter shaft portion 41 on the proximal end side of the connection member 20a is formed with an external diameter such that small-diameter shaft portion 41 fits in the hole 39 in the cylindrical member 13, by pressing the proximal end face of the small-diameter shaft portion 41 to the holding member 19 side with a jig or the like, the convex distal end portion 42 can be adjusted so as to abut (contact) against the outer circumferential face of the holding member 19 with an appropriate amount of force.

For example, a configuration may be adopted in which the length (in the axial direction) of the shaft portion 40 at which the diameter increases in a stepped shape from the small-diameter shaft portion 41 is made slightly smaller than a distance d between the outer circumferential face of the holding member 19 and the inner circumferential face of the cylindrical member 13, and after the holding member 19 is disposed inside the cylindrical member 13, the small-diameter shaft portion 41 is finely adjusted so that the holding member 19 is held with an appropriate amount of force in a state in which the holding member 19 is disposed along the central axis O.

Accordingly, the present embodiment can hold the holding member 19 along the central axis O in a well-balanced condition in which the amounts of force that hold the holding member 19 at a plurality of positions which are rotationally symmetric are all equal.

In this case, if the cylindrical member 13 and the holding member 19 can be machined with relatively good precision, a configuration may be adopted in which only one or two of the four connection members are made adjustable, and the aforementioned length in the other connection members is made equal to the distance d. Further, only the one or two connection members may be adjusted so as to hold the holding member 19 with equal amounts of force among all the connection members.

Figure 6:
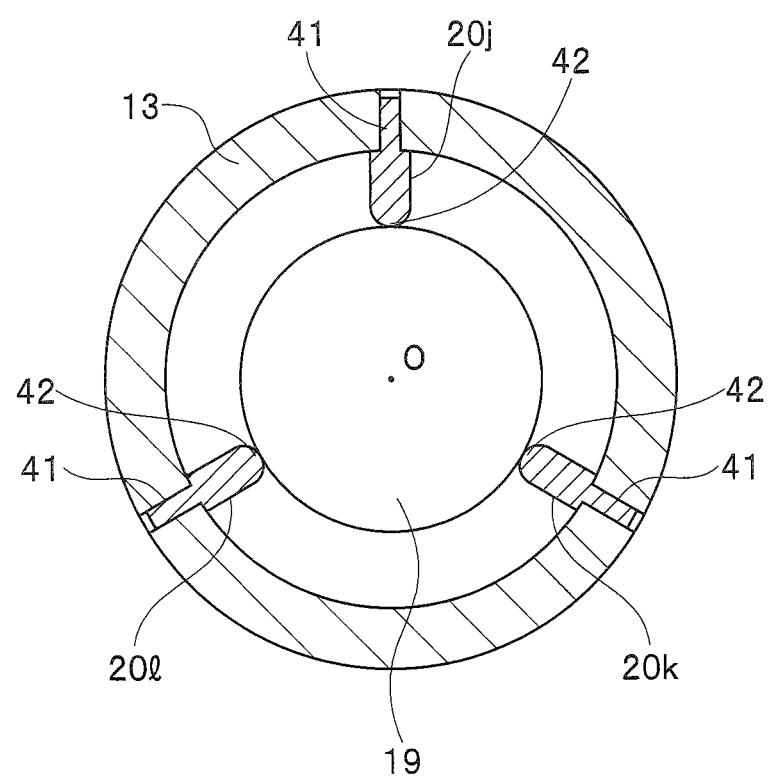
FIG. 6 is a transverse cross-sectional view illustrating the internal configuration of a cylindrical member in a scanning endoscope according to a first modification of the first embodiment.

Note that, although in the present embodiment a configuration is adopted so as to provide the connection members 20a to 20d and 20e to 20h at four places in the circumferential direction, as illustrated in a first modification shown in FIG. 6 a structure may also be adopted that holds the holding member 19 at three places that are rotationally symmetric in the circumferential direction.

For example, the connection members 20a to 20d at the position along the cross-section B-B in FIG. 2 may be changed to three connection members 20j to 20l at three places that are rotationally symmetric in the circumferential direction, as in the first modification illustrated in FIG. 6. Similarly, the connection members 20e to 20h may be changed to three connection members (not shown) that are rotationally symmetric.

When the holding member 19 is held at three places, although the strength with which the holding member 19 is held decreases in comparison to holding the holding member 19 at four places, the influence of vibrations can be decreased more. Therefore, whether to adopt a structure that holds the holding member 19 at four places or a structure that holds the holding member 19 at three places may be decided by taking into consideration the holding strength obtained by the connection members that are actually used and the influence of vibrations on images that are acquired.

In addition, to reduce the influence of vibrations, a configuration may be adopted in which, for example, the connection members 20a to 20d that hold the holding member 19 at the first prescribed location in FIG. 2 and the connection members 20e to 20h that hold the holding member 19 at the second prescribed location hold the holding member 19 using two connection members, respectively. Specifically, a configuration may be adopted so as to hold the holding member 19 at the first prescribed location in FIG. 2 by means of, for example, the two connection members 20*a* and 20*b* that oppose each other in the vertical direction, and to hold the holding member 19 at the second prescribed location by means of the connection members 20*g* and 20*h* that oppose each other in the lateral direction. Alternatively, a configuration may be adopted so as to hold the holding member 19 at the first prescribed location in FIG. 2 by means of the two connection members 20*c* and 20*d* that oppose each other in the lateral direction, and to hold the holding member 19 at the second prescribed location by means of the connection members 20*e* and 20*f* that oppose each other in the vertical direction.

Figure 7A:
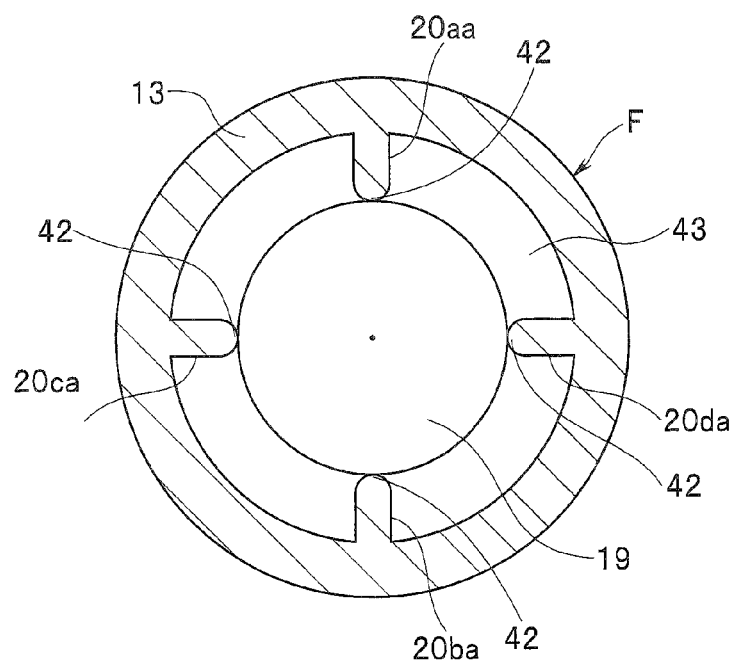
FIG. 7A is a transverse cross-sectional view illustrating the internal configuration of a cylindrical member in a scanning endoscope according to a second modification of the first embodiment.
Figure 7B:
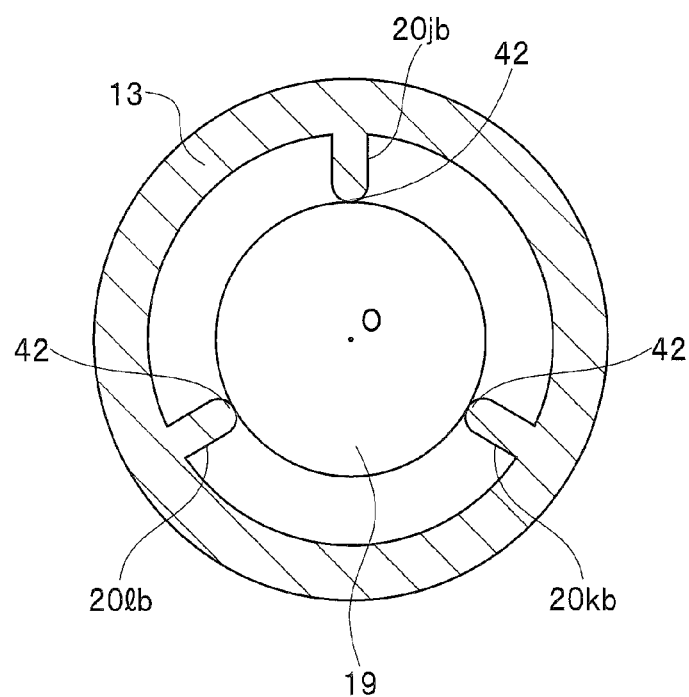
FIG. 7B is a transverse cross-sectional view illustrating the internal configuration of a cylindrical member in a scanning endoscope according to a third modification of the first embodiment.

Further, although in the examples illustrated in FIG. 5A, FIG. 5B, FIG. 6, and the like, a configuration is described in which the respective connection members 20*i* are provided on the cylindrical member 13 side (so as to protrude from the inner circumferential face (inner wall) of the cylindrical member 13) as separate members from the cylindrical member 13, the respective connection members 20*i* may be formed integrally with the cylindrical member 13, as in a second modification and a third modification that are illustrated in FIG. 7A and FIG. 7B, respectively.

FIG. 7A illustrates a structure in which the respective connection members 20*i* in FIG. 5A are changed to connection members 20*ia* that are formed integrally with the cylindrical member 13. For example, the connection members 20*a* to 20*d* in FIG. 5A become connection members 20*aa* to 20*da* in FIG. 7A. Each connection member 20*ia* protrudes to the center side in the radial direction from the inner circumferential face (inner wall) of the cylindrical member 13, with the distal end of each connection member 20*ia* being formed as the convex distal end portion 42, and the convex distal end portion 42 contacts or abuts against the outer circumferential face of the holding member 19 in a state that is close to point contact to thereby hold the holding member 19.

In the structure illustrated in FIG. 7B, the respective connection members 20*i* (i=j to l) in FIG. 6 are changed to connection members 20*ib* that are formed integrally with the cylindrical member 13.

In a case in which the connection members are integrated with the cylindrical member 13 as shown in FIG. 7A or FIG. 7B, the scanning endoscope can be manufactured at a lower cost in comparison to when the connection members are formed as separate members. Apart from this point, these integrated structures have substantially the same advantageous effects as the first embodiment.

In the first embodiment and the modifications of the first embodiment that are described above, a structure is described in which the holding member 19 is held by connection members provided on the cylindrical member 13 side. However, a structure may also be adopted in which the holding member 19 is held (by the cylindrical member 13) using connection members provided (so as to protrude from an outer circumferential face (outer wall) of the holding member 19) on the holding member 19 side as shown in a fourth modification illustrated in FIG. 8 and FIG. 9.

Figure 8:
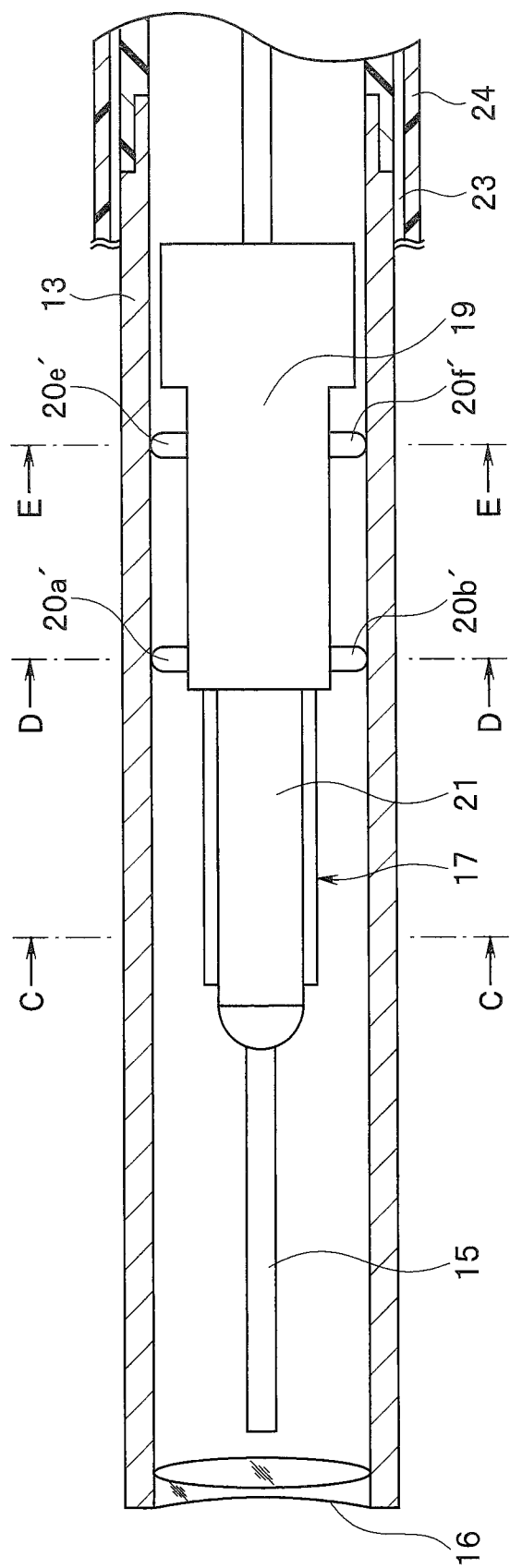
FIG. 8 is a longitudinal cross-sectional view illustrating the internal configuration of a cylindrical member in a scanning endoscope according to a fourth modification of the first embodiment.
Figure 9:
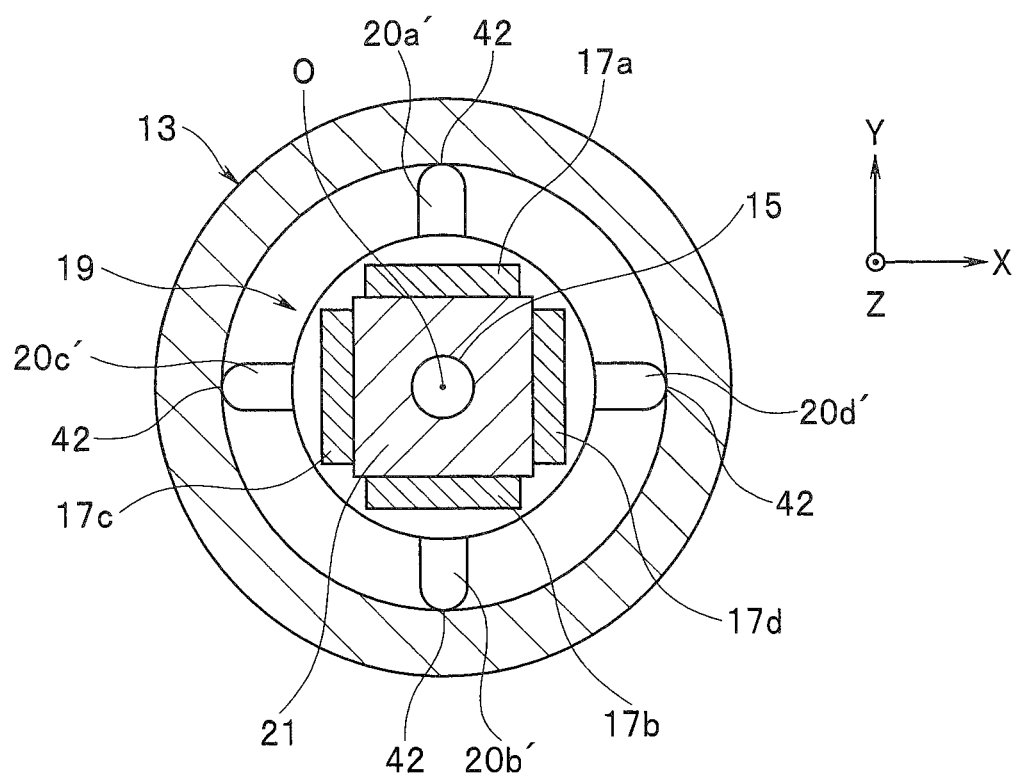
FIG. 9 is a cross-sectional view along a line C-C in FIG. 8.

FIG. 9 illustrates a cross-sectional view along a line C-C in FIG. 8. In the present modification, at the first prescribed location and the second prescribed location, connection members 20*i*' are provided at four places in the circumferential direction on the outer circumferential face of the holding member 19 that are rotationally symmetric about the central axis O. For example, the connection member 20*a* shown in FIG. 2 and FIG. 3 corresponds to a connection member 20*a*' in FIG. 8 and FIG. 9. The other connection members also correspond in a similar manner. The connection members 20*i*' are integrally formed by the same member as the holding member 19. This structure can suppress the influence on a scanning operation of the actuator 17 in a similar manner to the first embodiment. Further, the scanning endoscope can be manufactured at a low cost similarly to the case illustrated in FIG. 7A. Note that the connection members 20*i*' may also be formed as separate members from the holding member 19.

In the above described first embodiment and the first to third modifications, structures are adopted in which the proximal end side of each of the connection members 20*i* or the like is provided at the cylindrical member 13, and the convex distal end portion 42 of each of the connection members 20*i* protrudes towards the central axis O side along the radial direction and contacts or abuts against the outer circumferential face of the holding member 19. In contrast, in the present modification, the proximal end side of each of the connection members 20*i*' is provided on the holding member 19, and the convex distal end portion 42 of each of the connection members 20*i*' protrudes in a direction away from the central axis O along the radial direction and contacts or abuts against the inner circumferential face of the cylindrical member 13.

Figure 10A:
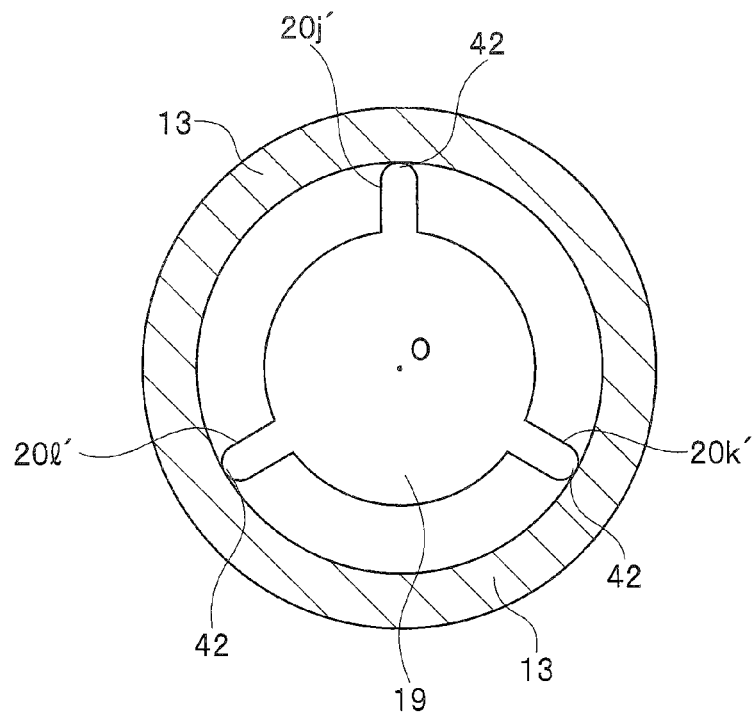
FIG. 10A is a transverse cross-sectional view illustrating an internal configuration of a cylindrical member at a first prescribed location in a fifth modification.

Further, although in the example illustrated in FIG. 9 a case is shown in which the connection member 20*a*' to 20*d*' are provided at four places at the first prescribed location, as illustrated in a fifth modification shown in FIG. 10A, a structure may also be adopted in which connection members are provided at three places in the circumferential direction on the outer circumferential face of the holding member 19 that are rotationally symmetric about the central axis O.

Note that the configuration illustrated in FIG. 10A shows, for example, connection members 20*i*' (i=j to l) that correspond to connection members 20*j* to 20*l* in FIG. 6 that are shown in an enlarged view at a cross-section along a line D-D in FIG. 8 or at a cross-section along a line B-B in FIG. 2. In FIG. 10A, similarly to the case in FIG. 6, an inner portion of the cross-section of the holding member 19 is omitted from the illustration (the same also applies with respect to FIG. 10B described hereunder).

Figure 10B:
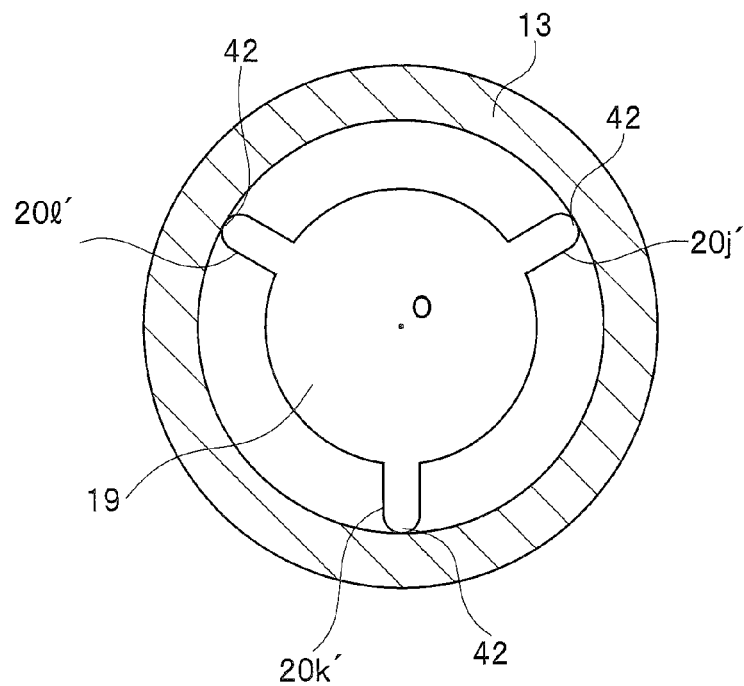
FIG. 10B is a transverse cross-sectional view illustrating an internal configuration of a cylindrical member at a second prescribed location in the fifth modification.

As shown in FIG. 10A, the connection members 20*i*' are provided integrally with the holding member 19. Further, connection members shown in an enlarged view of a cross-section along a line E-E as the second prescribed location in FIG. 8 may be provided as shown in FIG. 10B. The connection members 20*i*' shown in FIG. 10B match connection members provided at positions on the outer circumferential face of the holding member 19 in a state in which the connection members 20*i*' shown in FIG. 10A are rotated by 60° around the central axis O.

Naturally, the connection members may also be provided at positions on the outer circumferential face of the holding member 19 that are the same as in the case of the cross-section illustrated in FIG. 10A. Note that a configuration may also be adopted so as to provide connection members at two places, respectively, as the connection members provided at the first prescribed location and the second prescribed location. In this case, the connection members may be provided so as to be in the same relation as that described above for the case of two places.

Thus, with respect to the connection members provided at the first prescribed location and the second prescribed location, other connection members may be provided at positions on the holding member 19 that are reached when one of the connection member sides is rotated about the central axis O by an appropriate angle (as a specific example, 90° in the case of connection members provided at two places, for example 0° or 60° in the case of connection members provided at three places, or for example 0° or 45° in the case of connection members provided at four places). This arrangement may also be applied to the cases where the connection members are provided at positions on the outer circumferential face on the cylindrical member 13 side that are described above.

That is, with respect to the connection members provided at the first prescribed location and the second prescribed location, a configuration may also be adopted so as to provide other connection members at positions on the inner circumferential face of the cylindrical member 13 that are reached when one of the connection member sides is rotated about the central axis O by an appropriate angle.

Note that, although in the aforementioned example a case is described in which two to four connection members are provided as the number of connection members provided in the circumferential direction, the number of connection members may be greater, for example, may be from five to eight, or may also be nine or more.

Further, although in the above examples cases are described in which the connection members are provided at two locations in the longitudinal direction of the cylindrical member 13 or the holding member 19, the number of locations may be increased to three to four, or may also be five locations or more. In addition, although in the above examples cases are described in which the distal end on the opposite side to the proximal end of each connection member is a protrusion-type shape that has the convex distal end portion 42, various shapes that decrease the holding area can be adopted as shown in FIGS. 11A to 11C.

Figure 11A:
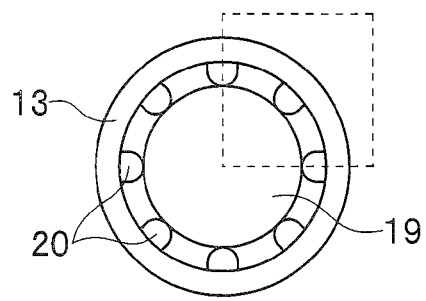
FIG. 11A is a front view with respect to FIG. 11B of a scanning endoscope of a sixth modification.
Figure 11B:
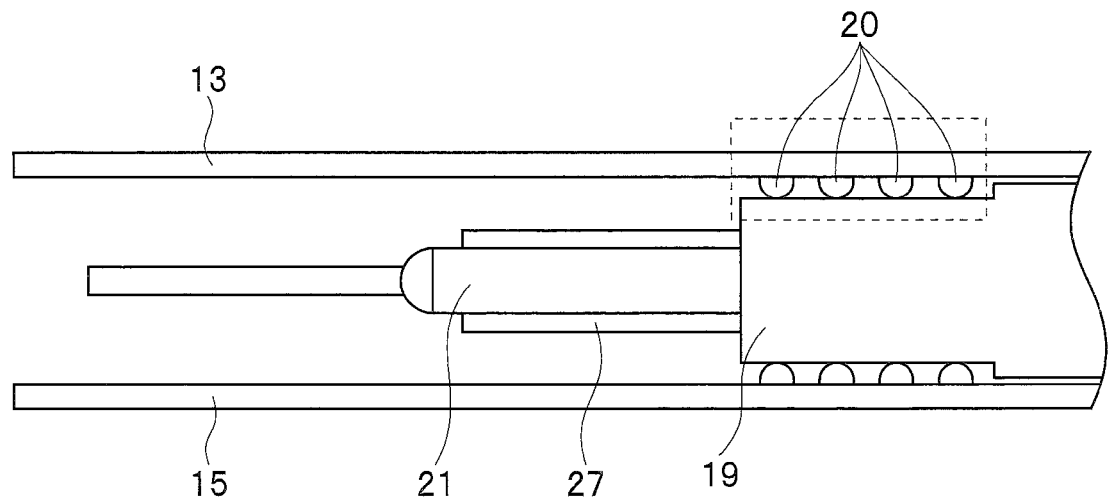
FIG. 11B is a view illustrating a schematic longitudinal section of the scanning endoscope of the sixth modification.

FIG. 11A illustrates the relation between the cylindrical member 13, the holding member 19 and the connection members 20 interposed between the cylindrical member 13 and the holding member 19 when seen from the front face in FIG. 11B. FIG. 11B illustrates the relation between the cylindrical member 13, the holding member 19 and the connection members 20 interposed between the cylindrical member 13 and the holding member 19 at a longitudinal cross-section that is similar to the case illustrated in FIG. 2. Note that the illumination lens 16 is omitted from the illustrations in FIG. 11A and FIG. 11B. Further, hatching of the cross-sectional structure is omitted in FIG. 11A and FIG. 11B.

In a sixth modification illustrated in FIG. 11A and FIG. 11B, connection members (denoted by reference numeral 20) are provided at eight places on the inner circumferential face of the cylindrical member 13 at four prescribed locations, respectively, in the longitudinal direction of the cylindrical member 13 and the holding member 19.

Figure 11C:
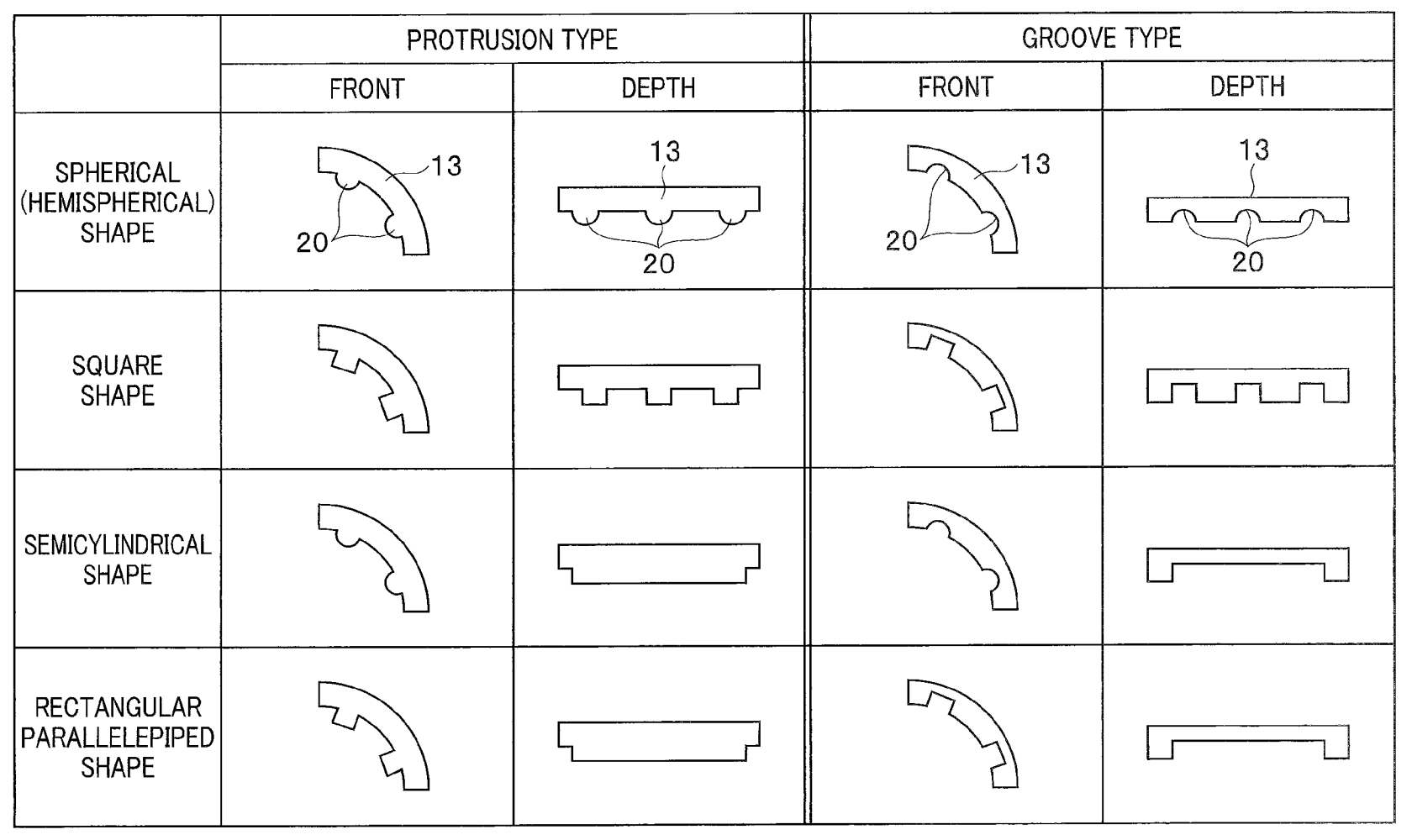

FIG. 11C is a view illustrating the modification shown in FIG. 11A and FIG. 11B in a simplified manner by means of a tabular format, and shows the cylindrical member 13 and connection member 20 within a frontal region and a depth region that are indicated by dashed lines, respectively.

As shown in a first row at the uppermost part in FIG. 11C, a configuration may be adopted in which connection members that are formed in a hemispherical (spherical) shape or, as shown on the right side of FIG. 11C, connection members formed as groove-type members by forming a hemispherical groove or concave portion in the inner circumferential face of the cylindrical member 13 may be adopted as the protrusion-type connection members 20 that protrude from the inner circumferential face of the cylindrical member 13.

Note that, in a case where the connection members are formed as groove-type members, the inner circumferential face at which a groove or concave portion is not formed serves as a portion which contacts or abuts against the holding member 19. Note that, in FIG. 11C, reference numerals are shown only in the case of hemispherical shapes, and are omitted in other cases.

Further, as shown in a second row that is adjacent to the first row on the underside of the first row in FIG. 11C, a configuration may also be adopted in which connection members that are formed in a square shape or, as shown on the right side of FIG. 11C, connection members formed as groove-type members by forming a square groove or concave portion in the inner circumferential face of the cylindrical member 13 may be adopted as the protrusion-type connection members 20 that protrude from the inner circumferential face of the cylindrical member 13.

Furthermore, as shown in a third row that is adjacent to the second row on the underside of the second row in FIG. 11C, a configuration may be adopted in which connection members that are formed in a semicylindrical shape or, as shown on the right side of FIG. 11C, connection members formed as groove-type members by forming a semicylindrical groove or concave portion in the inner circumferential face of the cylindrical member 13 may be adopted as the protrusion-type connection members 20 that protrude from the inner circumferential face of the cylindrical member 13.

In addition, as shown in a fourth row that is adjacent to the third row on the underside of the third row in FIG. 11C, a configuration may be adopted in which connection members that are formed in a rectangular parallelepiped shape or, as shown on the right side of FIG. 11C, connection members formed as groove-type members by forming a rectangular parallelepiped-shaped groove or concave portion in the inner circumferential face of the cylindrical member 13 may be adopted as the protrusion-type connection members 20 that protrude from the inner circumferential face of the cylindrical member 13.

Note that, although in FIG. 11C an example is illustrated in which the connection members 20 are provided on the cylindrical member 13 side, configurations may also be adopted in which the connection members 20 shown in FIG. 11C are provided on the holding member 19 side as shown in FIG. 8, FIG. 9, FIG. 10A and FIG. 10B.

Embodiments constituted by partially combining the above described embodiments and the like also belong to the present invention.

What is claimed is:

1. A scanning endoscope, comprising:
   a light guide configured to guide an illuminating light that is emitted from a light source, and irradiate an object with the illuminating light;
   an actuator configured to be driven so as to cause a distal end of the light guide to scan the illuminating light that is guided from the light guide over the object;
   a holder configured to hold the actuator;
   a tubular member configured to enclose the light guide, the actuator and the holder within a space defined by the tubular member; and
   a plurality of connectors interposed between the tubular member and the holder, wherein the plurality of connectors are configured to:
      hold the holder at a prescribed position inside the tubular member; and change shape in a circumferential direction which takes a longitudinal direction of the light guide as an axis when the tubular member or the holder receives a force.

2. The scanning endoscope according to claim 1, wherein the plurality of connectors are intermittently provided so as to contact an outer circumferential face of the holder or an inner circumferential face of the tubular member, at a plurality of positions that are rotationally symmetric in the circumferential direction.

3. The scanning endoscope according to claim 1, wherein the actuator is configured to be driven so as to cause the distal end of the light guide to scan the illuminating light that is guided from the light guide in a spiral shape over the object.

4. The scanning endoscope according to claim 1, wherein a first group of the plurality of connectors are provided at a plurality of positions that are rotationally symmetric with respect to the axis and are in a circumferential direction at a first location in a longitudinal direction of the tubular member, and wherein a second group of the plurality of connectors are provided at a plurality of positions that are rotationally symmetric with respect to the axis and are in a circumferential direction at a second location that is different from the first location in the longitudinal direction of the tubular member.

5. The scanning endoscope according to claim 1, wherein the plurality of connectors are provided at an inner circumference of the tubular member.

6. The scanning endoscope according to claim 1, wherein the plurality of connectors are provided at an outer circumference of the holder.

7. The scanning endoscope according to claim 1,
wherein the tubular member has a cylindrical shape,
wherein the holder has a cylindrical shape that holds the actuator and also holds the light guide that is disposed along a central axis, and
wherein each of the plurality of connectors comprises: a shaft that has a shape that is rotationally symmetric in a radial direction that is orthogonal to a central axis of the tubular member; and a convex surface provided at an end of the shaft, wherein the convex surface abuts against an outer circumferential face of the holder that has the cylindrical shape or an inner circumferential face of the tubular member that has the cylindrical shape, and holds the holder.

8. The scanning endoscope according to claim 7, further comprising an illumination lens configured to converge the illuminating light that is emitted from the light source, and to emit the illuminating light that is converged toward the object,
wherein a distal end of the tubular member is configured to hold the illumination lens.

* * * * *